US011117071B2

(12) United States Patent
Lucas

(10) Patent No.: US 11,117,071 B2
(45) Date of Patent: Sep. 14, 2021

(54) EXPANDED DISTILLATION FOR ETHANOL PRODUCTION

(71) Applicant: LucasE3, L.C., Shawnee, KS (US)

(72) Inventor: Scott A. Lucas, De Soto, KS (US)

(73) Assignee: LucasE3, L.C., Shawnee, KS (US)

( * ) Notice: Subject to any disclaimer, the term of this patent is extended or adjusted under 35 U.S.C. 154(b) by 0 days.

(21) Appl. No.: 16/935,673

(22) Filed: Jul. 22, 2020

(65) Prior Publication Data

US 2020/0346131 A1 Nov. 5, 2020

Related U.S. Application Data

(63) Continuation-in-part of application No. 15/991,835, filed on May 29, 2018, now abandoned.

(60) Provisional application No. 62/478,550, filed on Mar. 29, 2017.

(51) Int. Cl.
  *B01D 3/00* (2006.01)
  *B01D 71/02* (2006.01)
  *B01D 5/00* (2006.01)
  *C07C 29/80* (2006.01)

(52) U.S. Cl.
  CPC ............. *B01D 3/005* (2013.01); *B01D 3/007* (2013.01); *B01D 5/006* (2013.01); *B01D 5/0093* (2013.01); *B01D 71/028* (2013.01); *C07C 29/80* (2013.01); *B01D 2201/06* (2013.01); *B01D 2257/80* (2013.01)

(58) Field of Classification Search
  None
  See application file for complete search history.

(56) References Cited

U.S. PATENT DOCUMENTS

| 2,958,142 | A  | 11/1960 | Kershaw et al. |
| 3,363,340 | A  | 1/1968  | McKinley       |
| 3,673,705 | A  | 7/1972  | Wright et al.  |
| 4,309,254 | A  | 1/1982  | Dahlstrom      |
| 5,178,543 | A  | 1/1993  | Semans et al.  |
| 5,354,203 | A  | 10/1994 | Kotch et al.   |
| 7,504,546 | B2 | 3/2009  | Brown et al.   |
| 7,867,365 | B2 | 1/2011  | Brown          |

(Continued)

OTHER PUBLICATIONS

Katzen, et al., "Ethanol Distillation: the Fundamentals", 1999, 270-273.

*Primary Examiner* — Derek N Mueller
(74) *Attorney, Agent, or Firm* — Law Office of Mark Brown, LLC; Mark E. Brown

(57) ABSTRACT

A system and method for expanding the production capacity of an existing ethanol production facility including: a source of fermented mash (beer); a first beer column configured for receiving beer input from the source and for producing overhead comprising alcohol vapor and water vapor; and a first rectifier receiving an alcohol and water mixture from said first beer column. The system includes a second beer column, first and second condensers receiving overhead from the beer columns and a second rectifier receiving condensed overhead from the second condenser and bottoms from the first rectifier. A processing component receives bottoms from the first and second beer columns and steam condensate. The method includes the steps of retrofitting an existing ethanol production facility with a second beer column, first and second condensers and a second rectifier.

20 Claims, 2 Drawing Sheets

(56) References Cited

U.S. PATENT DOCUMENTS

| | | |
|---|---|---|
| 7,988,580 B2 | 8/2011 | McCrary |
| 8,173,412 B2 | 5/2012 | Dale |
| 9,308,489 B2 | 4/2016 | Brown et al. |
| 9,931,582 B2 | 4/2018 | Furlong |
| 2011/0315541 A1* | 12/2011 | Xu .......................... B01D 3/40 |
| | | 203/18 |
| 2014/0238881 A1 | 8/2014 | Stuhlmann et al. |
| 2014/0343259 A1 | 11/2014 | Bleyer et al. |
| 2015/0041305 A1 | 2/2015 | Overheul et al. |
| 2016/0279560 A1 | 9/2016 | Furlong |
| 2018/0290073 A1 | 10/2018 | Brown et al. |
| 2020/0171404 A1 | 6/2020 | Lucas |

* cited by examiner

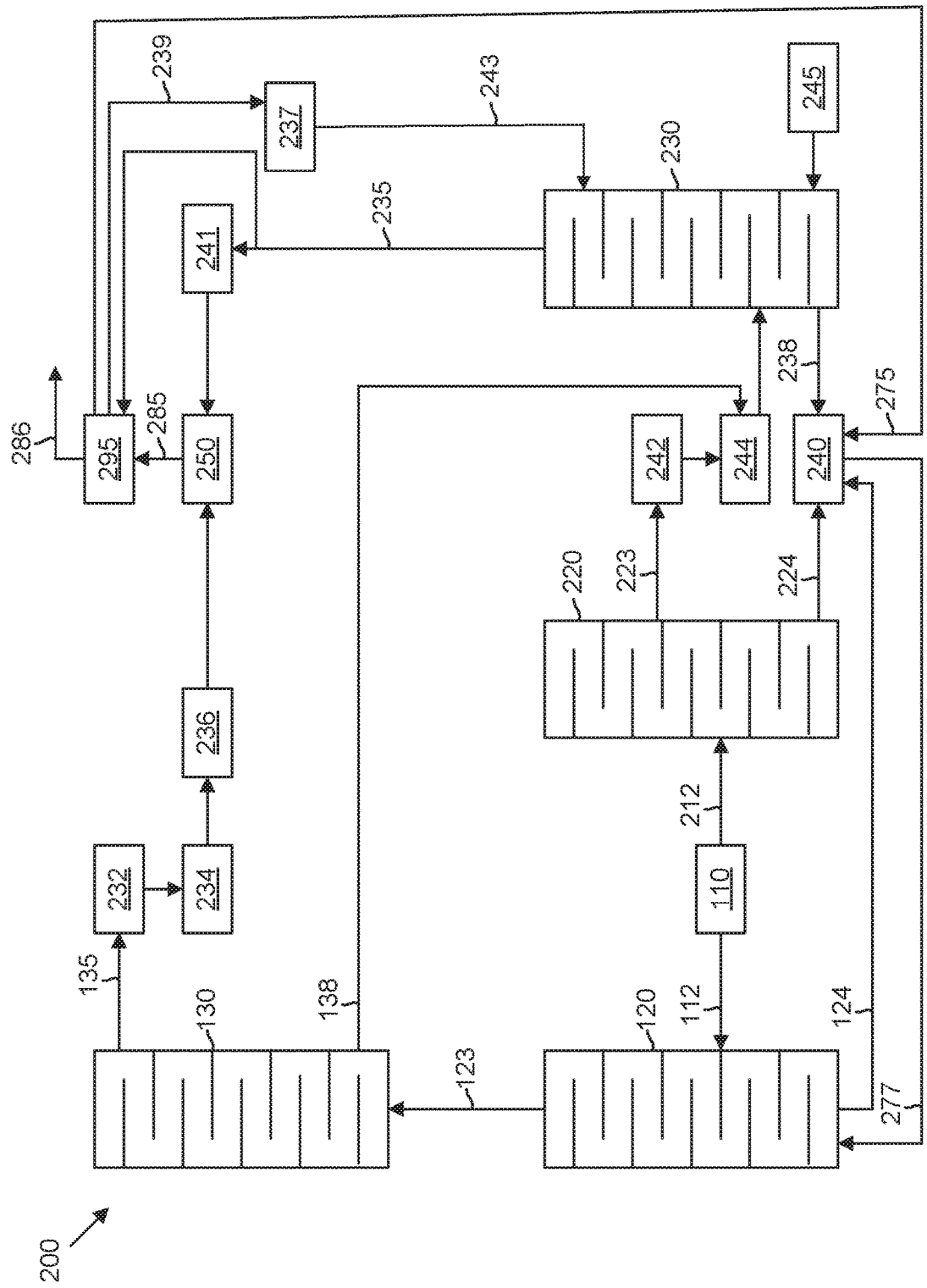

EXPANDED DISTILLATION FOR ETHANOL PRODUCTION

CROSS-REFERENCE TO RELATED APPLICATION

This application is a continuation-in-part of and claims priority in U.S. patent application Ser. No. 15/991,835, filed May 29, 2018, which claims priority in U.S. Provisional Patent Application No. 62/478,550, filed Mar. 29, 2017, and No. 62/623,459, filed Jan. 29, 2018, which are incorporated herein by reference.

BRIEF SUMMARY OF THE INVENTION

Ethanol has become an increasingly popular fuel source. Because ethanol can be produced from a variety of plant sources, it is a renewable energy source with positive effects on the environment relative to petroleum-based fuels. A common feedstock used for ethanol production within the United States is grain, although other inputs may be used in ethanol production. While providing environmental advantages over petroleum-based fuels, ethanol fuels still possess many of the advantages of petroleum-based fuels, such as the ability to power appropriately configured internal combustion engines and to be distributed in a liquid form. Ethanol may be used as a fuel source by itself or as part of a blend. Even if blended with petroleum-based fuels, the inclusion of ethanol in a fuel blend reduces the consumption of petroleum, which may be desirable for environmental, financial, and/or other reasons. Because of the popularity of ethanol, existing ethanol plants would benefit from expanded production capacity.

In order for an expansion of production at an existing ethanol plant to be feasible, the expanded capacity must be accomplished within the limiting parameters of the existing plant. The output of an ethanol plant may be limited by the physical footprint of the facility, the production capacity of the equipment already installed, and/or the processing of byproducts (such as heat). Simply adding production equipment to an existing ethanol plant may not be possible in some instances, and even when adding production equipment may be possible the addition requires the integration of that equipment into the systems and methods of that plant.

BRIEF DESCRIPTION OF THE DRAWINGS

The drawings constitute a part of this specification and include exemplary embodiments of the present invention illustrating various objects and features thereof.

FIG. 2 is a schematic diagram illustrating an ethanol production system and process with expanded capacity and other improvements comprising the present invention.

DETAILED DESCRIPTION OF THE PREFERRED EMBODIMENTS

I. Introduction and Environment

Figure 1:
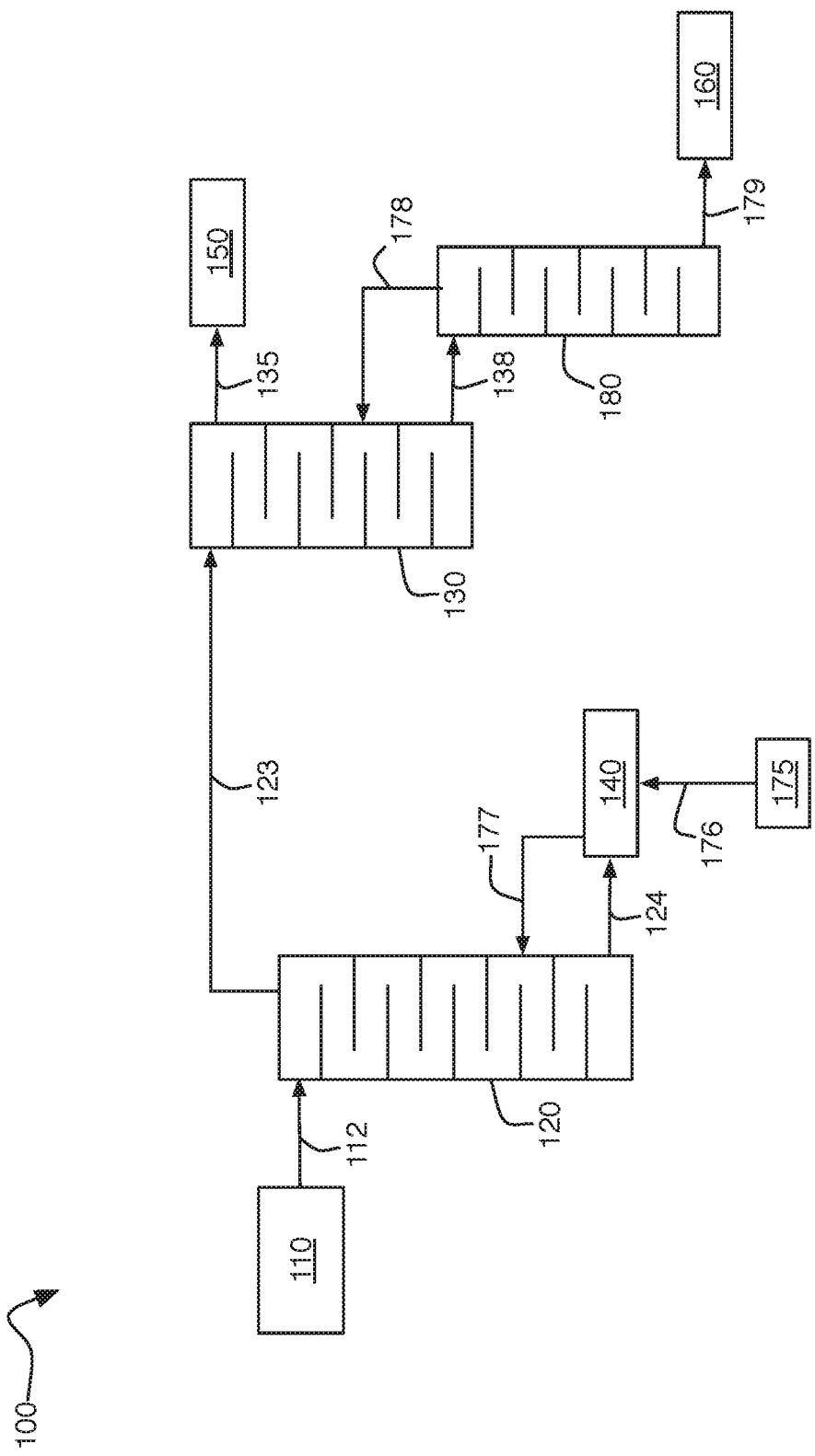
FIG. 1 is a schematic diagram illustrating a simplified example of a portion of a prior art conventional ethanol production system and process.

As required, detailed aspects of the present invention are disclosed herein, however, it is to be understood that the disclosed aspects are merely exemplary of the invention, which may be embodied in various forms. Therefore, specific structural and functional details disclosed herein are not to be interpreted as limiting, but merely as a basis for the claims and as a. representative basis for teaching one skilled in the art how to variously employ the present invention in virtually any appropriately detailed structure.

Certain terminology will be used in the following description for convenience in reference only and will not be limiting. For example, up, down, front, back, right and left refer to the invention as orientated in the view being referred to. The words, "inwardly" and "outwardly" refer to directions toward and away from, respectively, the geometric center of the aspect being described and designated parts thereof. Forwardly and rearwardly are generally in reference to the direction of travel, if appropriate. Said terminology will include the words specifically mentioned, derivatives thereof and words of similar meaning.

II. Preferred Embodiment Ethanol Distillation Method

Systems and methods in accordance with the present invention permit the production of ethanol by an existing plant to be increased within the limiting parameters of the plant. For example, a second beer column and a second rectifier column may be added to an existing plant, with the production of the second beer column and second rectifier column being limited by the capacity to utilize the heat generated by the second rectifier column in conducting the other processes of the ethanol plant. The second, additional beer column may produce less output than the first, previously existing beer column, but the net result will still be a net increase in the ethanol production of the plant.

FIG. 1 illustrates a simplified example 100 of a portion of a conventional ethanol production system and process. Ethanol production uses yeast(s) to ferment the sugars in grain(s) or other inputs to produce alcohol. Fermentation of grains may produce a beer 110. System 100 may isolate the alcohol within beer 110 for fuel, industrial, or other use. Beer 110 may have an alcohol content of between 8% and 16% by volume, dependent upon the sugar content of the input(s) used and the completeness of fermentation. Beer 110 may be input 112 into a beer column 120. Beer column 120 may pass the input 112 beer 110 through a series of trays while evaporating the alcohol and some water from the beer. The bottoms 124 of the beer column may comprise mostly water and solids, which may be processed 140 for re-use in system 100 using steam 175 input 176 into the bottoms processing system 140. An output 177, the overhead 123 of the beer column 120, may comprise a mixture of alcohol vapor and water vapor.

Beer column overhead 123 may be input into a rectifier 130 to further isolate the alcohol from the remaining water vapor. The bottoms 138 of the rectifier may comprise mostly water and some alcohol. Bottoms 138 may be processed by a stripping column 180 to separate the water 160 from the alcohol. The overhead 178 from stripping column 180 may contain alcohol from bottoms 138 and some water. The stripper overhead 178 may be sent to rectifier column 130 for further processing. The water 179 may be re-used in system 100 through processing 160. The overhead 135 from rectifier 130 may comprise mostly alcohol vapors and may be processed 150 to further concentrate the alcohol.

While the ethanol production systems such as the example shown in FIG. 1 can be operated in a profitable and efficient fashion, modifications to such an exemplary system may increase the production capacity within the existing spatial and energy limits of the pre-existing system. An example of such a modification in accordance with the present invention is illustrated in the example of FIG. 2.

As shown in the example 200 of FIG. 2, the pre-existing beer supply 110 may be input 112 to the pre-existing beer column 120 and may further be input 212 int© a second beer column 220. As in the example of FIG. 1, the pre-existing beer column 120 may output overhead 123 comprising a mixture of alcohol vapor and water vapor and bottoms 124 comprising mostly water and some solids. The second beer column 220 may be sized and/or operated at a capacity to operate within the pre-existing size and energy limitations of the ethanol production facility, such as described further below in examples. Second beer column 220 may be installed within the spatial limitations of a pre-existing ethanol production facility. Second beer column 220 may pass beer 212 through a series of trays to produce overhead 223 comprising alcohol vapor and water vapor and bottoms 224 comprising mostly water and solids. Bottoms 124, 224 may be combined and fed for processing 240. Vapors 275 from the new vapor condensing system 295 may be diverted to processing 240 to provide energy to replace steam, such as steam 175 used in the example of FIG. 1. An output, water vapors 277 from processing 240, may be used as an energy input for beer column 120 and/or beer column 220.

Still referring to the example 200 of FIG. 2, the overhead 123 from the preexisting beer column 120 may be input into the first rectifier 130. The overhead 135 from first rectifier 130 may comprise mostly alcohol vapors (such as 95% alcohol or 190 proof) that may be condensed 232, collected and pumped 234, then vaporized 236 prior to being passed to a molecular sieve 250 to output anhydrous alcohol vapor 285 that is condensed in the vapor condensing system 295 to produce steam 275 and the condensate for vapors 285 collected as anhydrous ethanol product 286. The bottoms 138 of the first rectifier 130 may be further processed as described herein.

Still referring to FIG. 2, the overhead 223 from the second beer column 220 may be input into a second rectifier 230. The overhead 223 from the second beer column 220 may be condensed 242 and collected and pumped 244 before being input into a second rectifier 230. Bottoms 138 from first rectifier 130 may be added to collected overhead 223 from second beer column for processing by second rectifier 230 as well. Second rectifier 230 may receive steam 245 and may operate at a higher pressure than first rectifier 130. The overhead 235 vapors from second rectifier 230 may be superheated with a heat exchanger 241 to ensure that no liquid droplets are contained within the overhead 235, which may then comprise mostly alcohol vapor, such as 95% alcohol or 190 proof and may be input, directly or indirectly, into a molecular sieve 250. The overhead 235 may be input into the molecular sieve 250 to produce anhydrous alcohol 285. A portion of overhead 235 may be routed to the vapor condensing system 295, which may use steam condensate to absorb heat from the vapors. The vaporized steam condensate 275 may then be used as an energy input for the bottoms processing system. Condensate from vapors 235, 239 is collected in 237 and pumped back to the second rectifier 230 as reflux 243.

Molecular sieve(s) 250 used may produce one hundred percent (200 proof) alcohol vapors 285. Those vapors 285 may be routed to the vapor condensing system 295 that uses steam condensate to absorb heat from the vapors. The vaporized steam condensate may then be used as an energy input for processing 240 to feed the first effect evaporators elsewhere in the ethanol production facility. The resulting condensed 200 proof ethanol liquid 286 may be collected for processing and use or sale.

Bottoms 238 of second rectifier 230 may comprise a mixture of water and alcohol, but in examples may comprise a sufficiently high percentage of water such that the bottoms 238 may be processed 240 by re-used as cooking water earlier in the ethanol production process.

As in the example of FIG. 1 shows, steam 175 may be input 176 in order to process 140 the bottoms, but as the example of FIG. 2 show, processes combined bottoms 124 from the first beer column 120 and bottoms 224 from the second beer column 220, output of the vapor condensing system 295 may be input 275 to further drive the processing 240 of the combined bottoms.

The modification of the example system 100 of FIG. 1 to the example system 200 of FIG. 2 may increase the overall capacity of ethanol production facility without significantly increasing the space required for the facility or the energy consumed by the facility. The transformation from a system such as the example system 100 of FIG. 1 to the example system 200 of FIG. 2 may be accomplished in a variety of ways. For example, the beer supply 110 may provide two separate inputs for the first beer column 120 and the second beer column 220 respectively, or a single input may be split between the first beer column 120 and the second beer column 220.

While described in examples herein, the present invention is not limited to such examples. Systems and methods in accordance with the present invention may be used to increase the output of a variety of pre-existing ethanol production facilities, regardless of the feedstock used and regardless of the previously installed equipment. By adding a beer column, particularly in place of a previously existing side stripper column, and by further replacing the side stripper column with a second rectifier operated at a higher pressure than the first rectifier, the production of an existing ethanol production facility may be increased within the existing constraints of the facility. As described herein, the additional beer column and the additional rectifier may be operated so as to enable the heat output from the second beer column to be used elsewhere and to avoid increasing either the energy demands of the system or the physical space required to operate the system.

While the vapors produced by a first rectifier and a second rectifier in systems and/or methods in accordance with the present invention may be processed using one or more molecular sieves to produce anhydrous alcohol, as described in examples herein, the overhead vapors by the first and second rectifier may be processed in other ways. In some examples, the overhead vapors of the first rectifier may be processed by different equipment and/or in a different fashion than the overhead vapors of the second rectifier.

Systems and methods in accordance with the present invention are described in examples herein as used for production of ethanol from grain, and any type of grain may be used for ethanol production in accordance with the present invention. In further examples, other types of feedstocks may be fermented to produce the beer distilled using systems and/or methods in accordance with the present invention.

In many examples of systems and methods in accordance with the present invention, additional equipment and processes beyond those described in examples herein will be used to produce a beer for distillation; to transport liquids, vapors, and solids during the fermentation and distillation process; to heat, cool, pressurize, de-pressurize or otherwise process materials as part of the ethanol production process; and/or to recycle or re-use the material and/or energy byproducts of various aspects of ethanol production. Such additional equipment and/or processes may be combined with systems and methods in accordance with the present invention. Further, additional modifications to conventional ethanol production systems and methods may be made in conjunction with systems and methods in accordance with the present invention.

Having thus described the invention, what is claimed as new and desired to be secured by Letters Patent is:

1. A method of expanding the production capacity of an existing ethanol production facility including: a source of fermented mash (beer); a first beer column configured for receiving beer input from said source and for producing overhead comprising alcohol vapor and water vapor, said first beer column also configured for producing bottoms comprising water and solids; and a first rectifier receiving an alcohol and water mixture from said first beer column, which method includes the steps of:
   providing a second beer column configured for receiving beer input from said source and for producing: overhead comprising alcohol vapor and water vapor; and bottoms comprising water and solids;
   providing a first condenser receiving overhead from said first rectifier, said first condenser providing alcohol output;
   providing a second condenser receiving said overhead from said second beer column;
   providing a second rectifier receiving: condensed overhead from said second condenser; and bottoms from said first rectifier; and
   providing a bottoms processing system receiving bottoms from said first and second beer columns and receiving boiler feed water.

2. The method according to claim 1, which includes the additional steps of:
   providing a vapor condensing subsystem configured for receiving overhead vapors from said second rectifier and providing steam as an input to said bottoms processing system; and
   feeding vaporized condensate to said bottom processing system.

3. The method according to claim 1, which includes the additional steps of:
   sizing and operating said second beer column within the pre-existing size and energy limitations of the existing ethanol production facility.

4. The method according to claim 2, which includes the additional step of:
   utilizing vapors from the bottom processing system to provide water vapors for one or both of the beer columns.

5. The method according to claim which includes the additional steps of:
   providing azeotropic water/alcohol vapor overhead from said first rectifier;
   condensing, collecting, pumping and vaporizing said water/alcohol vapor;
   passing said water/alcohol vapor to a molecular sieve to output anhydrous alcohol vapor; and
   condensing said anhydrous alcohol vapor in said vapor condensing subsystem to produce liquid anhydrous alcohol.

6. The method according to claim 1, which includes the additional steps of condensing, collecting and pumping the overhead from the second beer column before input into the second rectifier.

7. The method according to claim 6, which includes the additional steps of heating overhead vapors from the second rectifier to remove liquid, leaving substantially only alcohol vapor to feed the molecular sieves.

8. The method according to claim 7, which includes the additional steps of:
   routing a portion of the overhead from the second rectifier to the vapor condensing subsystem;
   said vapor condensing subsystem utilizing steam condensate to absorb heat from the vapors; and
   further utilizing said vaporized steam condensate as an energy input for said bottoms processing system.

9. The method according to claim 8, which includes the additional steps of:
   producing 99.8% wt to 99.0% wt alcohol vapors with a molecular sieve; and routing said alcohol vapors to the vapor condensing subsystem for absorbing heat with said condensate; and
   utilizing said vaporized steam condensate as energy input for said bottoms processing system.

10. The method according to claim 2, which includes the additional step of:
    providing a heat exchanger connected to and receiving overhead from said second rectifier;
    said heat exchanger connected to and providing alcohol vapor to said molecular sieve; and
    said heat exchanger configured for superheating overhead vapors to remove condensate liquid droplets, leaving only vapor to feed the molecular sieves.

11. In combination with an ethanol production facility including: a source of fermented mash (beer); a first beer column configured for receiving beer input from said source and for producing overhead comprising alcohol vapor and water vapor, said first beer column also configured for producing bottoms comprising water and solids; and a first rectifier receiving an alcohol and water mixture from said first beer column, the improvements comprising:
    a second beer column configured for receiving beer input from said source and for producing: overhead comprising alcohol vapor and water vapor; and bottoms comprising water and solids;
    a first condenser configured for receiving overhead from said first rectifier and providing alcohol output;
    a second condenser configured for receiving said overhead from said second beer column;
    providing a second rectifier receiving: condensed overhead from said second condenser; and bottoms from said first rectifier; and
    a bottoms processing system configured for receiving bottoms from said first and second beer columns and steam.

12. The invention according to claim 11, which includes:
    a vapor condensing subsystem configured for providing said vaporized condensate as an input to said bottoms processing system.

13. The invention according to claim 11 wherein said second beer column is sized and configured for operating within the pre-existing size and energy limitations of the existing ethanol production facility; and said second beer column is configured for condensing, collecting and pumping overhead therefrom to said rectifier.

14. The invention according to claim 11, which includes:
    a vapor condensing subsystem configured for receiving overhead from said second rectifier and providing steam as an input to said bottoms processing system.

15. The invention according to claim 11, which is configured for:
    said first rectifier providing azeotropic water/alcohol vapor overhead; and
    condensing, collecting, pumping and vaporizing, water/alcohol vapor overhead from said first rectifier, passing said, water/alcohol vapor overhead to a molecular sieve to output anhydrous alcohol vapor; and condensing said alcohol vapor in said vapor condensing subsystem to produce liquid alcohol.

16. The invention according to claim 11, which includes a heat exchanger for superheating overhead vapors from the second rectifier to remove condensate liquid droplets, leaving only vapor to feed the molecular sieves.

17. The invention according to claim 16 wherein a portion of the overhead from the second rectifier is routed to the vapor condensing subsystem; and said vapor condensing subsystem utilizes steam condensate to absorb heat from the vapors and further utilizes said vaporized steam condensate as an energy input for said bottoms processing system.

18. The invention according to claim 17, which includes:
    a molecular sieve configured for: producing 99.8% wt to 99.0% wt alcohol vapors and routing said alcohol vapors to the vapor condensing subsystem for absorbing heat with said condensate.

19. An ethanol production facility, which includes:
    a source of fermented mash (beer);
    a first beer column configured for receiving beer input from said source and for producing overhead comprising alcohol vapor and water vapor;
    said first beer column also configured for producing bottoms comprising water and solids;
    a first rectifier configured for receiving an alcohol and water mixture from said first beer column;
    a second beer column configured for receiving beer input from said source and for producing: overhead comprising alcohol vapor and water vapor; and bottoms comprising water and solids;
    a first condenser configured for receiving overhead from said first rectifier and providing alcohol output;
    a second condenser configured for receiving said overhead from said second beer column;
    a second rectifier configured for receiving condensed overhead from said second condenser and bottoms from said first rectifier; and
    a bottoms processing system configured for receiving bottoms from said first and second beer columns and steam condensate.

20. The invention according to claim 19, which includes:
    a molecular sieve configured for: producing 99.8% wt to 99.0% wt alcohol vapors and routing said alcohol vapors to the vapor condensing subsystem for absorbing heat with said condensate.

* * * * *